United States Patent
Lilja et al.

(10) Patent No.: US 9,919,077 B2
(45) Date of Patent: Mar. 20, 2018

(54) CO-PRECIPITATION OF A THERAPEUTIC AGENT INTO HYDROXYAPATITE COATINGS

(71) Applicant: Stryker European Holdings I, LLC, Kalamazoo, MI (US)

(72) Inventors: Mirjam Lilja, Farsta (SE); Philip Procter, Divonne les Bains (FR); Hartwig Steckel, Kiel (DE); Torben Christian Sörensen, Mönkeberg (DE); Jan Soerensen, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 6 days.

(21) Appl. No.: 14/897,352

(22) PCT Filed: Jun. 19, 2014

(86) PCT No.: PCT/IB2014/062454
§ 371 (c)(1),
(2) Date: Dec. 10, 2015

(87) PCT Pub. No.: WO2014/203204
PCT Pub. Date: Dec. 24, 2014

(65) Prior Publication Data
US 2016/0144070 A1 May 26, 2016

Related U.S. Application Data

(60) Provisional application No. 61/837,668, filed on Jun. 21, 2013.

(51) Int. Cl.
*A61L 27/32* (2006.01)
*A61L 27/54* (2006.01)
(Continued)

(52) U.S. Cl.
CPC ............... *A61L 27/32* (2013.01); *A61L 27/54* (2013.01); *A61L 31/086* (2013.01); *A61L 31/16* (2013.01); *A61L 2430/02* (2013.01)

(58) Field of Classification Search
None
See application file for complete search history.

(56) References Cited

U.S. PATENT DOCUMENTS

| 5,047,034 A | 9/1991 | Sohngen |
| 5,053,212 A | 10/1991 | Constantz et al. |

(Continued)

FOREIGN PATENT DOCUMENTS

| CN | 101537208 A | 9/2009 | |
| EP | 0806212 A1 * | 11/1997 | ......... A61F 2/30767 |

(Continued)

OTHER PUBLICATIONS

Habibovie et al. "Biomimetic Hydroxyapatite Coating on Metal Implants", (2002) J. Am. Ceram. Soc. 85 [3] 517-22. (Year: 2002).*

(Continued)

*Primary Examiner* — Carlos A Azpuru
*Assistant Examiner* — Casey S Hagopian
(74) *Attorney, Agent, or Firm* — Lerner, David, Littenberg, Krumholz & Mentlik, LLP

(57) ABSTRACT

A method for co-precipitating a therapeutic agent into a hydroxyapatite coated surface includes the steps of providing a surface and applying a hydroxyapatite seed layer on the surface. The hydroxyapatite seed layered surface is contacted with a solution including the therapeutic agent and a co-precipitated therapeutic agent, hydroxyapatite layer is formed on the coated surface to uniformly distribute the therapeutic agent in the layer. Further, an implant having sustained therapeutic agent delivery includes a base and an hydroxyapatite seed layer disposed on a surface of the base.

(Continued)

A co-precipitated hydroxyapatite coating is disposed on the seed layer. The coating includes a therapeutic agent, wherein the therapeutic agent is provided in a solution of therapeutic agent.

18 Claims, 14 Drawing Sheets

(51) Int. Cl.
*A61L 31/08* (2006.01)
*A61L 31/16* (2006.01)

(56) References Cited

U.S. PATENT DOCUMENTS

| | | |
|---|---|---|
| 5,164,187 A | 11/1992 | Constantz et al. |
| 5,188,670 A | 2/1993 | Constantz |
| 5,279,831 A | 1/1994 | Constantz et al. |
| 5,964,932 A | 10/1999 | Ison et al. |
| 5,968,253 A | 10/1999 | Poser et al. |
| 6,053,970 A | 4/2000 | Ison et al. |
| 6,558,709 B2 | 5/2003 | Higham |
| 6,596,338 B2 | 7/2003 | Scott et al. |
| 6,821,528 B2 | 11/2004 | Scott et al. |
| 7,507,483 B2 * | 3/2009 | Schwartz ............... B05D 1/185 148/254 |
| 2003/0049324 A1 | 3/2003 | Vogt et al. |
| 2003/0077381 A1 | 4/2003 | Scott et al. |
| 2006/0134160 A1 | 6/2006 | Troczynski et al. |
| 2007/0213832 A1 * | 9/2007 | Wen ....................... A61F 2/4455 623/23.5 |
| 2007/0259101 A1 | 11/2007 | Kleiner et al. |
| 2008/0306579 A1 | 12/2008 | Dolan et al. |
| 2009/0269480 A1 | 10/2009 | Berglund |

FOREIGN PATENT DOCUMENTS

| | | | |
|---|---|---|---|
| EP | 0806212 A1 * | 11/1997 | ......... A61F 2/30767 |
| WO | 2009100792 A2 | 8/2009 | |
| WO | 2010126436 A1 | 11/2010 | |
| WO | 2013013218 A2 | 1/2013 | |
| WO | 2013067049 A1 | 5/2013 | |
| WO | 2013072576 A1 | 5/2013 | |

OTHER PUBLICATIONS

Sörensen et al., "Biomechanical and antibacterial properties of Tobramycin loaded hydroxyapatite coated fixation pins", Journal of Biomedical Materials Research B: Applied Biomaterials, 2014, vol. 00B, Issue 00, 12 pages.

Sörensen et al., "Biomimetic Hydroxyapatite Coated Titanium Screws Demonstrate Rapid Implant Stabilization and Safe Removal In-Vivo", Journal of Biomaterials and Nanobiotechnology, 2015, 6, 20-35.

"Non-Toxic and Bio-Compatible Type 2 Titanium Anodizing", 2003, XP055117504, Retrieved from the Internet: <URL: http://www.danco.net/PDF-DOWNLOADS/TITANIUM I I. pdf>, [retrieved on May 12, 2014].

Aberg et al, Bisphosphonate incorporation in surgical implant coatings by fast loading and co-precipitation at low drug concentrations, J Mater Sci: Mater Med (2009) 20:2053-2061.

Abtahl et al, A bisphosphonate-coating improves the fixation of metal implants in human bone, A randomized trial of dental implants, Bone 50 (2012) 1148-1151.

Brohede et al, Multifunctional implant coatings providing possibilities for fast antibiotics loading with subsequent slow release, J Mater Sci: Mater Med (2009) 20:1859-1867.

Brunski et al, Biomaterials and Biomechanics of Oral and Maxillofacial Implants: Current Status and Future Developments, The Inrternational Journal of Oral & Maxillofacial Implants, 2000. 15-46.

F. Chai et al, Antibacterial activation of hydroxyapatite (HA) with controlled porosity by different antibiotics, Biomolecular Engineering 24 (2007) 510-514.

Forsgren et al, Co-loading of bisphosphonates and antibiotics to a biomimetic hydroxyapatite coating, Biotechnol Lett (2011) 33:1265-1268.

Hetrick et al, Reducing implant-related infections: active release strategies, I Chem. Soc. Rev., 2006, 35, 780-789.

Hutson et al, Infections in Periarticular Fractures of the Lower Extremity Treated with Tensioned Wire Hybrid Fixators, Journal of Orthopaedic Trauma vol. 12, No. 3, 1998, pp. 214-218.

International Search Report for Application No. PCT/EP2013/068082 dated May 26, 2014.

International Search Report for Application No. PCT/IB2014/060905 dated Jun. 26, 2014.

International Search Report for Application No. PCT/IB2014/062454 dated Sep. 29, 2014.

James M Anderson, Biological Responses to Materials, Annu. Rev. Mater. Res. 2001. 31:81-110.

Johan Forsgren et al, Formation and adhesion of biomimetic hydroxyapatite deposited on titanium substrates, Acta Biomaterialia 3 (2007) 980-984.

K.C. Baker et al, Growth, characterization and biocompatibility of bone-like calcium phosphate layers biomimetically deposited on metallic substrata, Materials Science and Engineering C 26 (2006) 1351-1360.

Lilja et al, Photocatalytic and antimicrobial properties of surgical implant coatings of titanium dioxide deposited though cathodic arc evaporation, Biotechnol Lett (2012) 34:2299-2305.

Liu et al, Water-based sol-gel synthesis ofhydroxyapatite: process development, Biomaterials 22 (2001) 1721-1730.

M.P. Ginebra et al, Calcium phosphate cements as bone drug delivery systems: A review, Journal of Controlled Release 113 (2006) 102-110.

Ma et al, Electrophoretic deposition of porous hydroxyapatite scaffold, Biomaterials 24 (2003) 3505-3510.

Mahan et al, Factors in Pin Tract Infections, Department of Orthopedic Surgery, University of Louisville, Louisville, Ky., Mar. 1991 vol. 14 No. 3 V , pp. 305-308.

Masse et al, Prevention of Pin Track Infection in External Fixation with Silver Coated Pins: Clinical and Microbiological Results, J Biomed Mater Res (Appl Biomater) 53: 600-604, 2000.

Poelstra et al, Prophylactic treatment of gram-positive and gram-negative abdominal implant infections using locally delivered polyclonal antibodies, Received: Jun. 15, 2000, pp. 206-215.

Sergio Allegrini Jr., et al, Hydroxyapatite grafting promotes new bone formation and osseointegration of smooth titanium implants, Ann Anat 188 (2006) 143-151.

Stigter M et al: "Incorporation of different antibiotics into carbonated hydroxyapatite coatings on titanium implants. release and antibiotic efficacy", Journal of Controlled Release, Elsevier, Amsterdam, NL, vol. 99, No. 1, Sep. 14, 2004 (Sep. 14, 2004). pp. 127-137, XP004549075.

Stigter M et al: "Incorporation of tobramycin into biomimetic hydroxyapatite coating on titanium", Biomaterials. Elsevier Science Publishers BV, Barking, GB, vol. 23, No. 20, Oct. 1, 2002 (Oct. 1, 2002), pp. 4143-4153. XP004370405.

Tengvalla et al, Surface immobilized bisphosphonate improves stainless-steel screw fixation in rats, Biomaterials 25 (2004) 2133-2138.

Ulrika Brohede et al: "Multifunctional implant coatings providing possibilities for fast antibiotics loading with subsequent slow release", Journal of Materials Science: Materials in Medicine, Kluwer Academic Publishers, BO, vol. 20, No. 9, Apr. 28, 2009 (Apr. 28, 2009) pp. 1859-1867, XP019730963.

Zilberman et al, Antibiotic-eluting medical devices for various applications, journal of Controlled Release 130 (2008) 202-215.

Szesz (Thin Solid Films 528 (2013) 163-166).

Habibovic (J. Am. Ceram. Soc., 85 [3] 517-22 (2002).

* cited by examiner

10μm

10μm

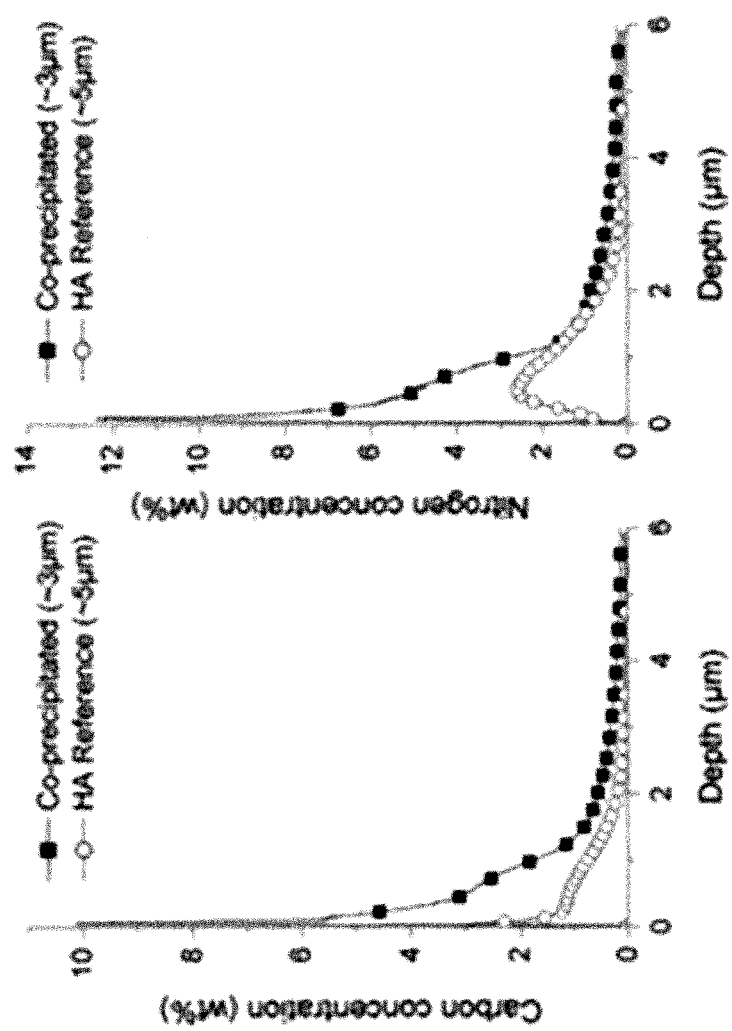

CO-PRECIPITATION OF A THERAPEUTIC AGENT INTO HYDROXYAPATITE COATINGS

CROSS-REFERENCE TO RELATED APPLICATIONS

The present application is a national phase entry under 35 U.S.C. §371 of International Application No. PCT/IB2014/062454 filed Jun. 19, 2014, published as WO 2014/203204 A1, which claims priority from U.S. Patent Application No. 61/837,668 filed Jun. 21, 2013, all of which are hereby incorporated herein by reference.

TECHNICAL FIELD

A method for co-precipitating a therapeutic agent into a hydroxyapatite coated surface of an implant.

BACKGROUND

The clinical fields of orthopedics and traumatology deal with the reconstruction and preservation of the injured musculoskeletal system and associated organs. Implant loosening, migration, cut-out, as well as, infection control play a major role in complications that may occur post-surgery. In general, hydroxyapatite (HA) is a common material used for biomedical applications. HA coatings are known to be biocompatible, osteoconductive and typically enhance osseointegration of implants and therefore contribute towards more rapid and enhanced fixation. See Allegrini S et al., "Hydroxyapatite Grafting Promotes New Bone Formation and Osseointegration of Smooth Titanium Implants" Ann Anat 188 143-51 (2006) and Baker K. et al., "Growth, Characterization and Biocompatibility of Bone-like Calcium Phosphate Layers Biomimetically Deposited on Metallic Substrata" Mater Sci Eng 26 1351-60 (2006).

Hydroxyapatite can be deposited onto surgical implants by different processes, such as, biomimetic deposition from aqueous solution, plasma-spraying, electrophoretic deposition, sol-gel processes or dip-coatings temperature, each resulting in process dependent coating characteristics. See Forsgren J. et al, Acta Biomater; Wang M. J. et al., "Electrophoretic Deposition of Porous Hydroxyapatite Scaffold" Biomaterials 24 3505-10 (2003) and Dean-Mo L. et al. "Water-based Sol-Gel Synthesis of Hydroxyapatite: Process Development" Biomaterials" 22 1721-30 (2001).

The nanoporous structure of biomimetic HA coatings have shown promising properties for drug incorporation and with respect to local drug delivery. See U.S. Provisional Patent Application No. 61/814,538. HA coatings can provide an excellent carrier for various water soluble drugs. See Forsgren J. et al., "Co-loading of Bisphosphonates and Antibiotics to a Biomimetic Hydroxyapatite Coating" Biotechnol Lett 33 1265-68 (2011).

The local release of drugs from calcium phosphate based materials and functional HA implants coatings enable favorable enhancement of local bone tissue regeneration in-vivo See Abtahi J. et al., "A Bisphosphonate-Coating Improves the Fixation of Metal Implants in Human Bone—A Randomized Trial of Dental Implants" Bone 50 1148-51 (2012) and Tengwall P. et al., "Surface Immobilized Bisphosphonate Improves Stainless-steel Screw Fixation in Rats" Biomaterials 25 2133-8 (2004), as well as to prevent early bacterial colonization and biofilm formation, see Ginebra M. et al., "Calcium Phosphate Cements as Bone Drug Delivery Systems: A Review" J Control Release 113 102-10 (2006).

Most approaches for incorporating drugs into porous calcium phosphates or HA coatings focus on adsorptive loading techniques from drug containing aqueous solutions. Incorporation of drugs into the porous HA coating structure can be done by soaking of the HA coated implant in the drug containing solution. See Brohede U. et al., "Multifunctional Implant Coatings Providing Possibilities For Fast Antibiotics Loading with Subsequent Slow Release" J Mater Sci-Mater Med 20 1859-67 (2009). To date an antibiotic release over a period of 8 days has been demonstrated from adsorption-loaded HA coatings deposited on fixation pins, while the longest antibiotic effect demonstrated so far does not exceed 3 days. See Lilja, M. et al., "Photocatalytic and Antimicrobial Properties of Surgical Implant Coatings of Titanium Dioxide Deposited Through Cathodic Arc Evaporation" Biotechno Lett 12 2299-305.2 (2012).

Co-precipitation, incorporating drugs simultaneously during biomimetic growth of the coating, in contrast, offers the possibility to incorporate drugs during coating growth and, hence, constitutes a promising method for producing functional drug containing coatings in a single step process. The drug concentration in the buffer solution, as well as, the chemical and molecular structure of the drug has been shown to be critical parameters impacting the coating growth and the drug content of such coatings. See Åberg J. et al., "Bisphosphonate Incorporation in Surgical Implant Coatings by Fast Loading and Co-precipitation at Low Drug Concentrations" J Mater Sci-Mater 20 2053-61 (2009). Thus, the initial nucleation and growth of drug-containing HA remains a challenging and not fully understood process step.

SUMMARY

In one embodiment, a method for co-precipitating a therapeutic agent into a hydroxyapatite coated surface includes the steps of providing a surface and applying a hydroxyapatite seed layer on the surface. The hydroxyapatite seed layered surface is contacted with a solution including the therapeutic agent and a co-precipitated therapeutic agent, hydroxyapatite layer is formed on the coated surface to uniformly distribute the therapeutic agent in the layer.

In another embodiment, a method for loading an implant with a therapeutic agent, includes the steps of providing an implant and applying a biomimetic hydroxyapatite seed layer on a surface of the implant. The hydroxyapatite seed layered implant is contacted with a solution including the therapeutic agent. A co-precipitated therapeutic agent, hydroxyapatite layer is formed on the coated implant to uniformly distribute the therapeutic agent in the layer.

In still another embodiment, an implant having sustained therapeutic agent delivery includes a base and an hydroxyapatite seed layer disposed on a surface of the base. A co-precipitated hydroxyapatite coating is disposed on the seed layer. The coating includes a therapeutic agent, wherein the therapeutic agent is provided in a solution of therapeutic agent.

The foregoing summary, as well as the following detailed description of the embodiments, will be better understood when read in conjunction with the appended drawings. It should be understood that the embodiments depicted are not limited to the precise arrangements and instrumentalities shown.

BRIEF DESCRIPTION OF THE DRAWINGS

FIGS. 8(a)-8(b) are GD-OES analyses of the HA seed layered co-precipitated samples carbon depth profile (FIG. 8(a)) and nitrogen depth profile (FIG. 8(b)).

DETAILED DESCRIPTION OF THE EMBODIMENT(S)

The present embodiments focus on incorporation of Tobramycin into biomimetic HA coatings using the co-precipitation approach. The impact of deposition temperature and drug concentration on coating growth on crystalline $TiO_2$ covered substrates is addressed. In order to overcome the problematic nucleation phase in the presence of high drug concentrations, the impact of a sub-micron thin HA-layer is evaluated. High pressure liquid chromography (HPLC) is employed to study the drug release properties of Tobramycin co-precipitated fixation pins and these properties are correlated to release profiles obtained from HA coatings loaded by passive adsorption.

Due to current problems during surgery, such as implant migration, loosening and cut-out, as well as nosocomial infections, new innovative strategies that overcome the above-identified issues of thin coatings and extra loading steps are needed. As fully set forth herein, the method of the present disclosure involves co-precipitation combining Tobramycin with biomimetic hydroxyapatite (HA) directly at the time of nucleation to produce novel implant coatings. Such Tobramycin-doped HA coatings may ensure controlled local drug delivery to prevent early bacterial colonization of the implant. A sub-micron thin HA layer served as seed layer for the co-precipitation process and allowed for incorporation of Tobramycin in the coating from a stock solution of antibiotics concentrations as high as 20 mg/ml. Concentrations from 0.5 to 20 mg/ml Tobramycin and process temperatures of 37° C. and 60° C. were tested to assess the optimal parameters resulting in a thin Tobramycin delivering HA coating on discs and fixation pins. The coating morphology and thickness, as well as, the release profile in a phosphate buffered solution were evaluated via scanning electron microscopy and high pressure liquid chromatography. The innovative approach to use a HA seed layer demonstrated the feasibility to manufacture a thin Tobramycin-doped HA coating showing controlled delivery of pharmaceutically relevant amounts of drug over a period of 12 days in-vitro above the minimal inhibitory concentration of *Staphylococcus aureus*.

Although Tobramycin is described, drug, pharmaceutical or therapeutic agent, as used herein, refers to, but in no way is limited to antibiotics, vitamins, chemotherapy drugs, bisphosphonates, strontium-ranelate, PTH, osteoporotic drugs, growth factors, or a combination thereof.

Figure 1:
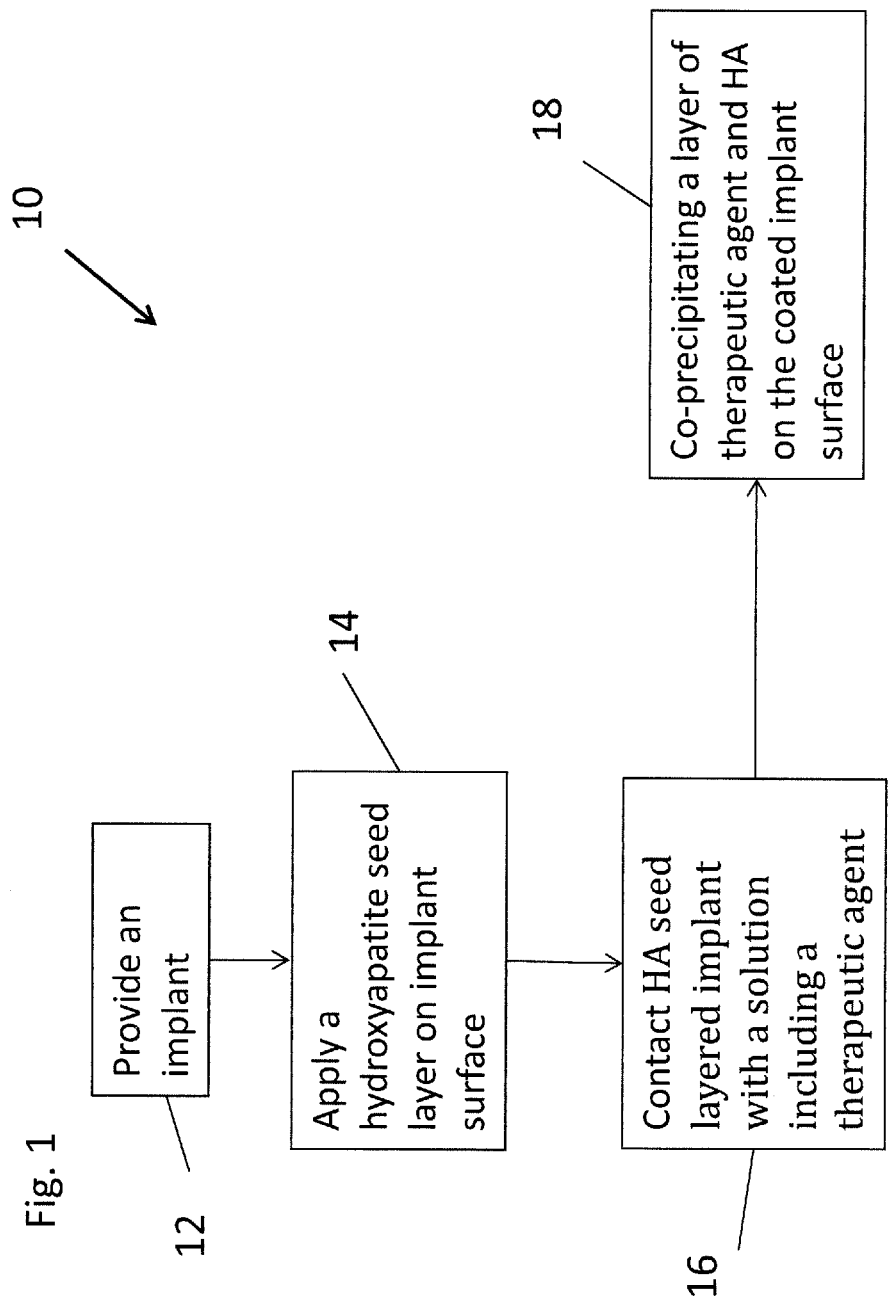
FIG. 1 is a flow diagram illustrating the method of the present disclosure.
Figure 2:
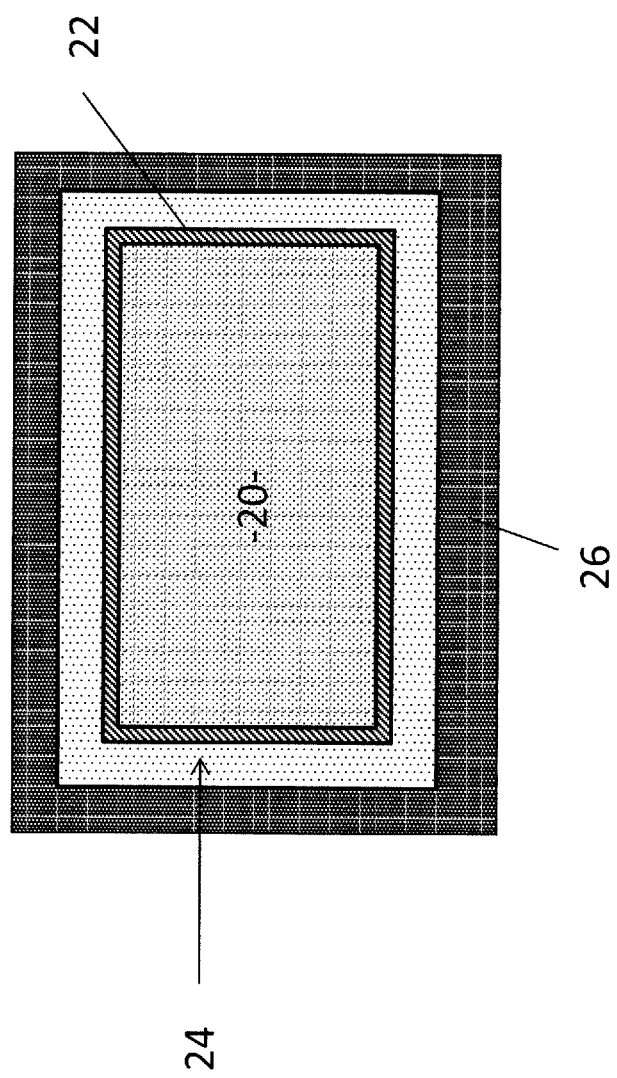
FIG. 2 is a cross-section of an implant made according to the method of the present disclosure.
Figure 3A:
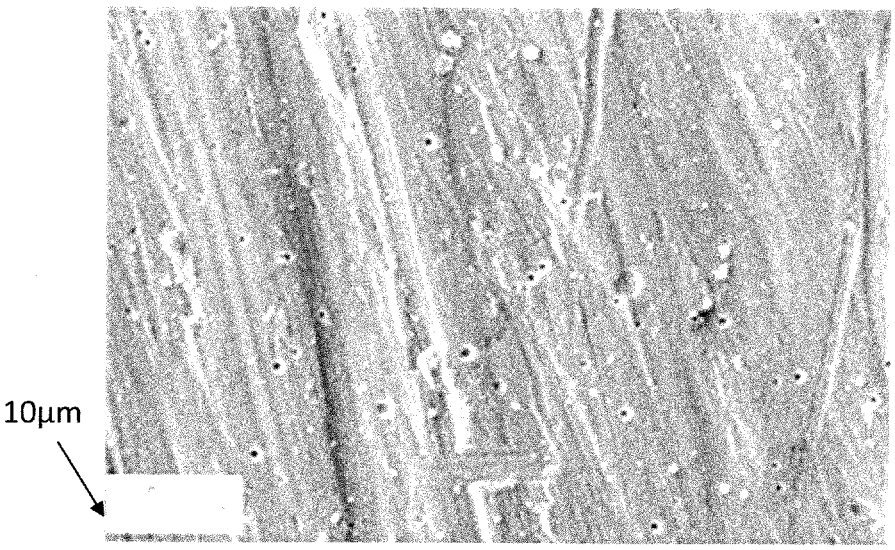
FIGS. 3(a)-3(d) are SEM images of the surface structures after immersion in Tobramycin containing PBS buffer for 6 days with a) 0.5 mg/ml Tobramycin at 37° C.; b) 1.0 mg/ml Tobramycin at 37° C.; c) 0.5 mg/ml Tobramycin at 60° C.; and d) 1.0 mg/ml Tobramycin at 60° C.
Figure 3B:
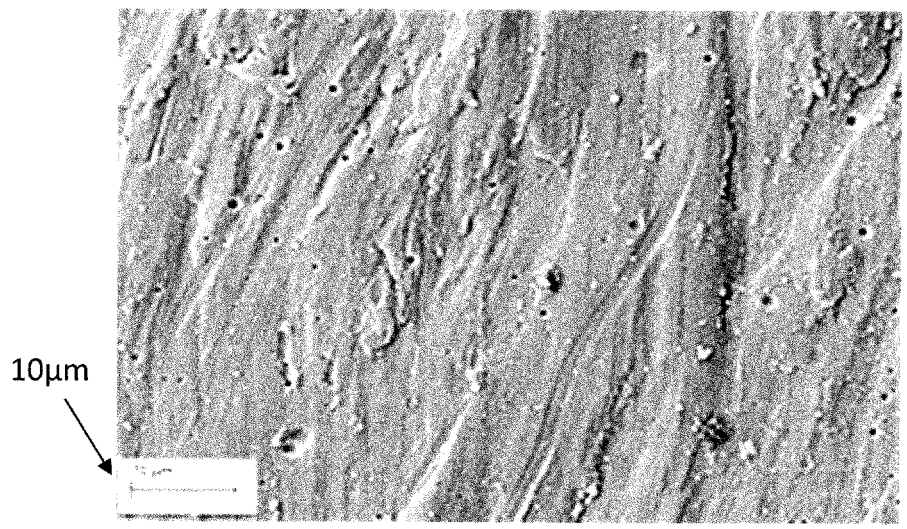
Figure 3C:
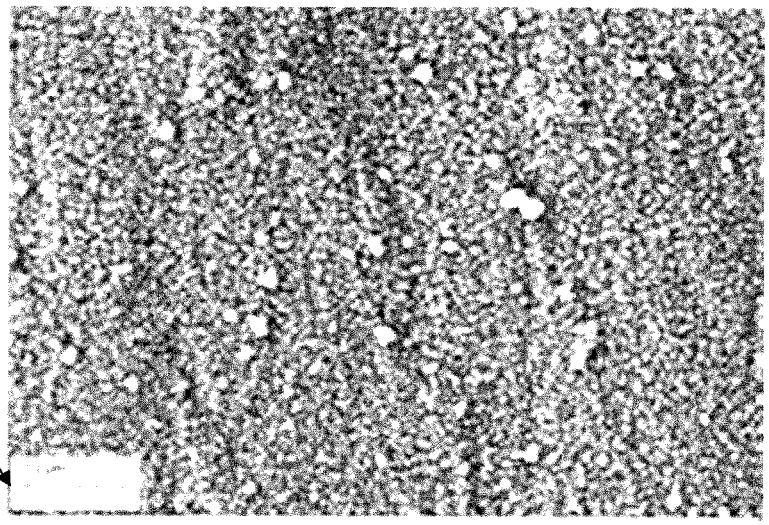
Figure 3D:
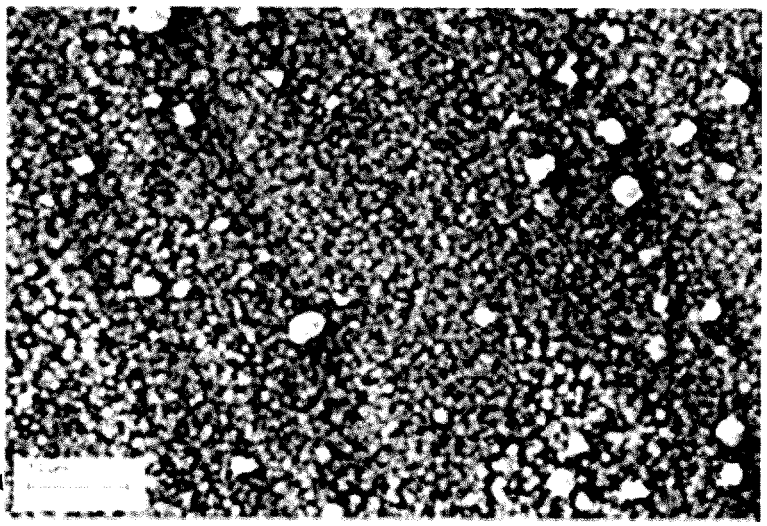

Referring to FIG. 1, a method 10 for co-precipitating a therapeutic agent into a hydroxyapatite coated surface includes a step 12 of providing a surface. As shown in FIG. 2, a surface 20 can be an implant or device. Implant, device and the like are used synonymously to refer to any object that is designed to be placed partially or wholly within a patient's body for one or more therapeutic purposes, such as for restoring physiological function, alleviating symptoms associated with disease, delivering therapeutic agents, and/or repairing or replacing or augmenting etc. damaged or diseased organs and tissues.

Representative examples of medical implants/devices include pins, fixation pins and other orthopedic devices selected from the group of implants, dental implants, stents, drug delivery devices, sheets, films, meshes, soft tissue implants, implantable electrodes, implantable sensors, drug delivery pumps, tissue barriers and shunts. It should be appreciated that other surfaces or devices can be used.

Implant 20 can include a base with a metal base coating 22 selected from the group of titanium, titanium alloy, nickel-titanium alloy, tantalum, platinum-iridium alloy, gold, magnesium, stainless steel, chromo-cobalt alloy, ceramics, biocompatible plastics or polymers and combinations thereof. For example, $TiO_2$, $TiO$, $TiCrO_2$, $Ti_2O_3$, $Ti_3O_5$, $SiO_2$, $MgO_2$, $AlO_2$, and $CrO_2$. Base coating 22 can be applied on implant 20 via cathotic arc evaporation. Other known coating methods can be employed.

Providing an implant made of Ti of any grade, and exposing this implant to air, results in the formation of a very thin, native, and often amorphous, $TiO_2$ coating. Despite its amorphous microstructure, this native $TiO_2$ coating has the ability to form HA coatings on its surface, especially at elevated PBS temperature (i.e., 60° C.). The surface chemistry is "responsible" for the ionic interactions with the ions of the PBS. At elevated temperatures, it is even possible to form HA on other oxides, such as MgO and $Al2O_3$. With such, the HA crystals usually form in the PBS solution and then collect on the substrate, which results in a HA coating.

Referring again to FIGS. 1 and 2, a hydroxyapatite seed layer 24 is applied on the implant in step 14. As discussed supra, the seed layer can be grown biomimetically. The biomimetic method includes soaking the implant in a simulated body fluid, such as a phosphate buffer saline (PBS), at an appropriate temperature and pH. The temperature of the solution can be, for example, 30-90° C. A conformed coating will be formed after a few days of soaking in the heated solution.

Seed layer 24 has a thickness of about 0.1 μm to about 1 μm. As will be described further herein, the thin HA seed layer triggers and/or enables the growth of a drug containing HA coating at high drug concentrations.

The PBS solution is prepared with various ion concentrations to mimic the chemical composition of human body fluids, such as blood plasma. The solution can contain calcium and phosphate ions. Moreover, the coating can be a substituted HA, where the substitution ions can be bone mineral relevant ions such as Si, Sr, Mg, CO2-3 and F.

In step 16 the hydroxyapatite seed layered surface is contacted with a solution including the therapeutic agent. The implant surface to be covered with therapeutic agent-doped HA is stored in aqueous phosphate buffered solution with addition of different amounts of agent. The therapeutic agent is released in the solution at specified concentration. For example, from about 0.5 to about 40 mg/ml.

In next step 18, a co-precipitated therapeutic agent, hydroxyapatite layer 26 is formed on the coated surface to uniformly distribute the therapeutic agent in the layer. Incorporating the drugs simultaneously during biomimetic growth of the coating, results in the co-precipitated HA-drug layer 26. The drug molecules are by use of this deposition method distributed uniformly throughout the coating thickness and consequently the drug release of such a co-precipitated coating, as described further herein, exhibits a controlled, sustained release profile. Co-precipitated layer 26 can be grown to a thickness of about 1 μm to about 10 μm. Co-precipitated layer 26 can also be an ion substituted hydroxyapatite. The substitution ions can be bone mineral relevant ions such as Si, Sr, Mg, CO2-3 and F.

The feasibility to co-precipitate the hydrophilic aminoglycoside antibiotic Tobramycin into HA-coatings while nucleation on the implant surface was evaluated. The impact of the different process parameters and pretreatments of the material on the nucleation and co-precipitation of Tobramycin-doped hydroxyapatite onto bioactive, crystalline $TiO_2$ coated stainless steel discs and fixation pins was noted. Additionally, to overcome the problematic starting phase of HA nucleation described above, pre-covering the surface by a nanoscaled HA-layer was evaluated. The HA seed layer seeds and triggers crystallization. Thus, by this approach, significantly higher amounts of Tobramycin can be co-precipitated to a drug-doped hydroxyapatite-coating by a more rapid approach compared to non HA seed layered surfaces. Additionally, pharmaceutically relevant doses of drugs can be released from this coating over a reasonable period of time. Furthermore, the special technique allowed the Tobramycin-doped HA coating to grow not only on planar geometries, but also on complex geometries like fixation pins.

Orthopedic grade stainless steel fixation pins (φ4 mm, 90 mm×30 mm) Stryker Trauma AG (Selzach, Switzerland) and circular discs (φ=9 mm, thickness 1 mm) of titanium grade 5 were used for coating deposition. Stainless steel plates (20 mm×20 mm×1 mm) of medical grade AISI type 316L served as substrates for glow discharge optical emission spectroscopy (GD-OES) investigations.

The substrates were coated with a crystalline, anatase $TiO_2$ coating through cathodic arc evaporation over a deposition time of 20 minutes. Co-precipitation of Tobramycin on the bioactive, crystalline $TiO_2$ coated substrates was performed by adding different amounts of antibiotic Tobramycin) to Dulbecco's Phosphate Buffered Saline (PBS) that serves as an ion source.

Following the cathodic arc deposition of the crystalline $TiO_2$, the substrates were ultrasonically cleaned in isopropanol and de-ionized water (5 min in each). Subsequently, the discs and plates were placed in plastic cups containing 20 ml of PBS, whereas the fixation pins were placed in plastic tubes containing 50 ml of PBS. Two test series were performed in order to investigate the influence of antibiotic concentration on coating growth, as well as, the impact of surface chemistry on the drug affinity. All samples for both test series were produced in triplicate. The first test series was performed on $TiO_2$ coated titanium discs. Different concentrations of Tobramycin (0.5 mg/ml; 1.0 mg/ml; 4 mg/ml; 20 mg/ml and 40 mg/ml) were added to PBS and the samples were stored for 6 days at 37° C. or 60° C.

The affinity of Tobramycin to different surface chemistries was evaluated by covering the TiO2 coated substrates prior to co-precipitation deposition with a sub-micron thin HA seed layer. The HA seed layer was obtained by immersion in PBS for 3 days at 60° C. For the second test series, discs with the HA seed layer were stored for 6 days in PBS at 60° C. containing Tobramycin at concentrations of 4 mg/ml and 20 mg/ml, respectively. Co-precipitated coatings on fixation pins with the HA seed layer were made by placing the pins for 6 days in PBS with Tobramycin concentrations of 4 mg/ml and 20 mg/ml at 37° C., producing samples denoted as Co-4 and Co-20, respectively. After the coating process all samples were air dried in an oven at 37° C. for 24 hours.

Additionally, the adsorptive loading properties of co-precipitated coating structures were evaluated. For this study Co-4 samples were placed for 5 minutes in round bottom test tubes (130 mm×14 mm×1 mm) containing 5 ml of room-tempered Tobramycin stock solution at a concentration of 20 mg/ml. The resulting samples were denoted Co-4/20. The coating homogeneity and thickness was evaluated via scanning electron microscopy (SEM) and the Tobramycin release from the fixation pins was evaluated using HPLC.

The biomimetically co-precipitated HA coatings were examined using a Zeiss Supra 40 Scanning Electron Microscope. SEM cross section images of the Tobramycin-doped HA obtained by ion milling (E-3500, Hitachi) was recorded to evaluate the thicknesses and structures of the deposited HA coatings. The coating thickness of the as-deposited coatings was evaluated at regions of flake-off, which were intentionally created on the surfaces using a razor blade.

To quantify the amount of drug released and in order to evaluate the release kinetics of Tobramycin eluting from Co-4, Co-20 and Co-4/20 samples, liquid chromatography (HPLC) was used. The methodology of all measurements were performed and modified according to the British Pharmacopoeia "HPLC Detection of Gentamicin Sulphate" Volume I 695-697 (1999); Fabre H. et al., "Determination of Aminoglycosides in Pharmaceutical Formulations—I. Thin layer Chromatography, *J Pharmaceut Biomed* 7 883-892 (1989); and Fabre H. et al., "Determination of Aminoglycosides in Pharmaceutical Formulations—II. High-Performance Liquid Chromotography"*J Pharmaceut Biomed* 17 1711-1718 (1989).

The presence and penetration depth of Tobramycin incorporated in the as-deposited, co-precipitated coatings were evaluated by glow discharge optical emission spectroscopy (GD-OES, GDA750-HP Spectruma Analytik GmbH, Germany). Quantitative profiles of Tobramycin characteristic elements nitrogen (N) and carbon (C) were obtained by measuring the chemical composition of antibiotic doped HA samples from the sample surfaces towards the substrate.

Referring to FIGS. 3(*a*)-3(*d*), SEM analyses of the surface structures after immersion in Tobramycin containing PBS buffer for 6 days with a) 0.5 mg/ml Tobramycin at 37° C.; b) 1.0 mg/ml Tobramycin at 37° C.; c) 0.5 mg/ml Tobramycin at 60° C.; d) 1.0 mg/ml Tobramycin at 60° C., are shown.

SEM analysis of sample surfaces from the first series produced at 37° C. and with Tobramycin concentrations of 4, 20 and 40 mg/ml, demonstrated no signs of HA nucleation on the crystalline $TiO_2$ coated discs. Lowering the Tobramycin concentration to 0.5 mg/ml or 1.0 mg/ml did not result in any observable HA nucleation, see FIGS. 3(*a*) and 3(*b*).

Increasing the temperature to 60° C., nucleation could be observed for the Tobramycin concentration of 0.5 mg/ml and 1.0 mg/ml clearly activated nucleation. See FIGS. 3(c) and 3(d). As shown, the HA coatings possess an inhomogeneous, rough, ball-like morphology covered with additional, ball-like agglomerates. The coating thickness was measured to be approx. 1.5 µm after storage for 6 days at 60° C. for both antibiotic concentrations. The thickness and appearance of all coating investigated are presented in Table 1.

Figure 4:
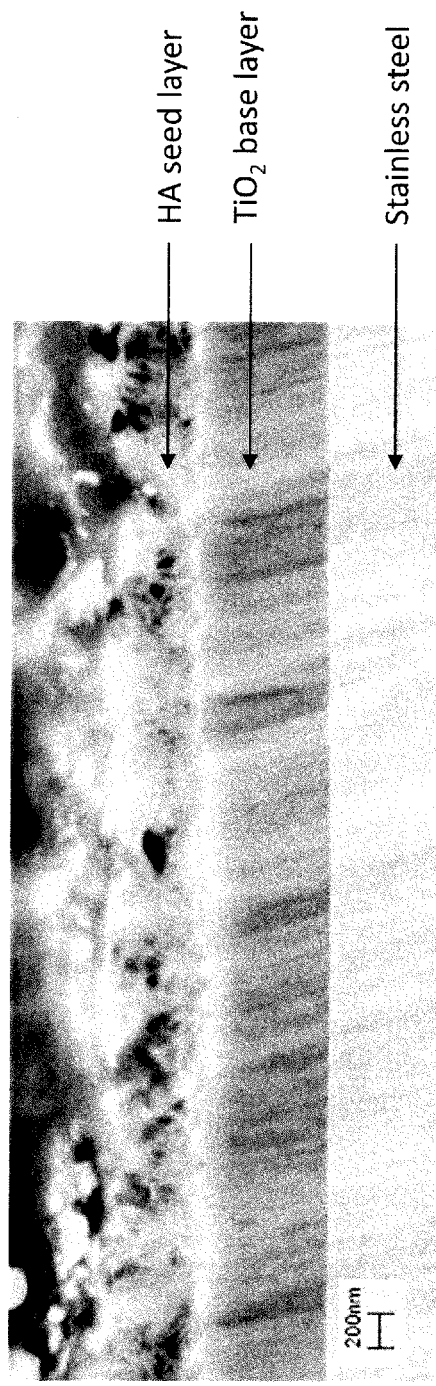
FIG. 4 is a cross-section of the HA seed layer after immersion for 3 days in PBS at 60° C.
Figure 5A:
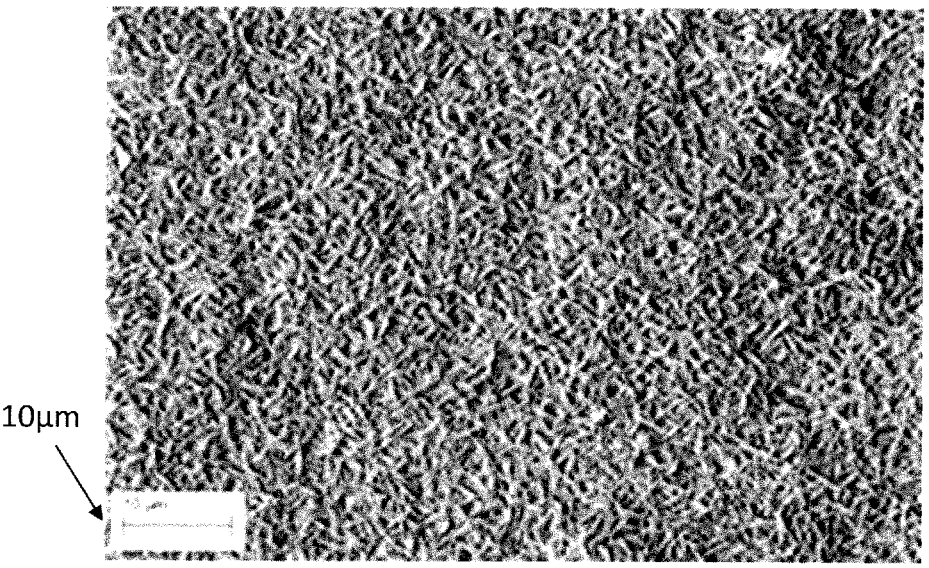
FIGS. 5(a)-5(b) are SEM images of the HA seed layered surface structures after immersion in Tobramycin-doped PBS for 6 days with a) 0.5 mg/ml Tobramycin at 37° C.; b) 1.0 mg/ml Tobramycin at 37° C.; c) 0.5 mg/ml Tobramycin at 60° C.; and d) 1.0 mg/ml Tobramycin at 60° C.
Figure 5B:
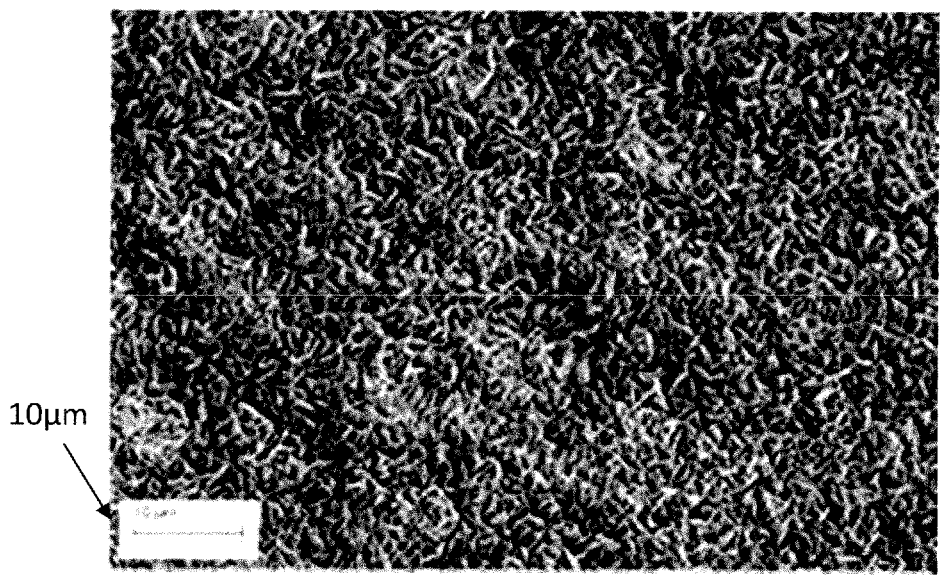
Figure 5C:
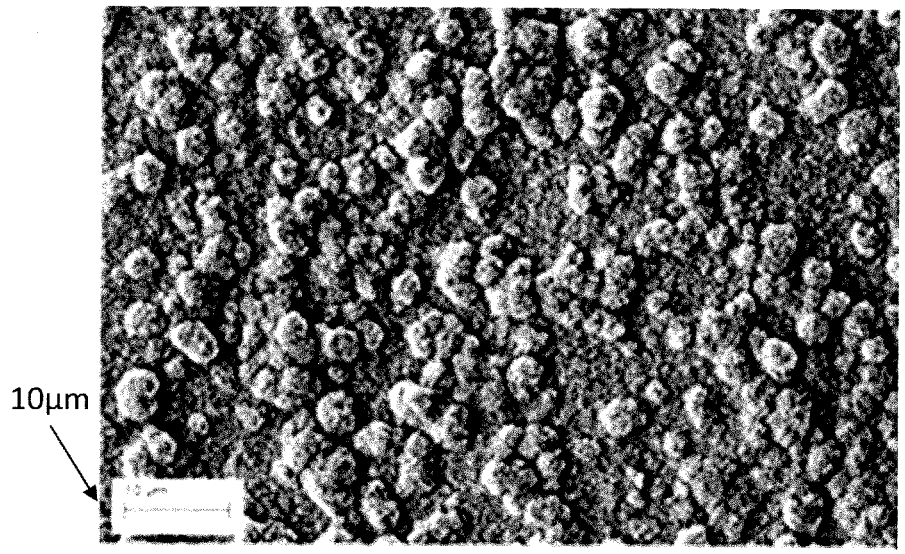
Figure 5D:
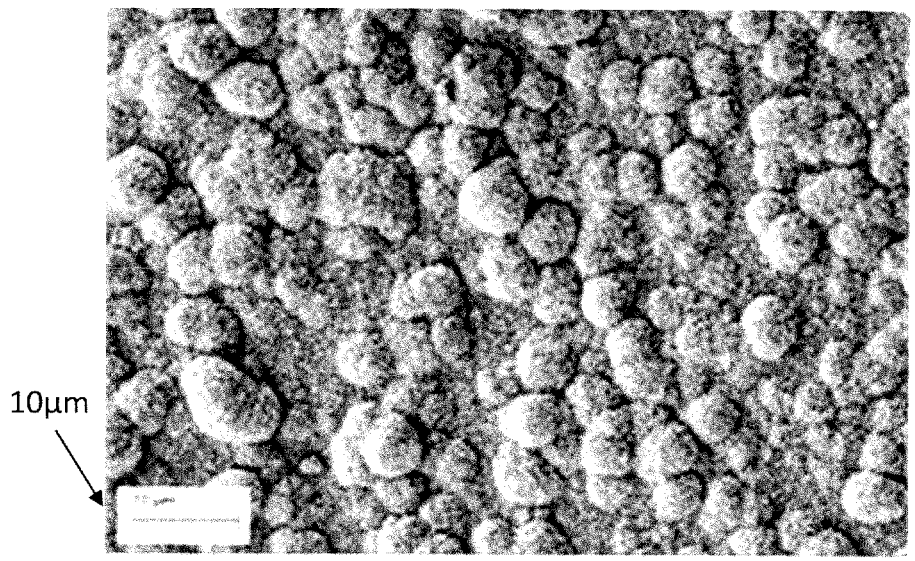

The second test series was performed on crystalline TiO$_2$ coated substrates that were additionally coated with an HA seed layer. As shown in FIG. 4, SEM cross-section analysis revealed an HA seed layer thickness in the range of about 300 to about 600 nm after immersion for 3 days in PBS at 60° C.

Referring to FIGS. 5(a)-5(d), growth of Tobramycin-doped hydroxyapatite coating could be observed for both concentrations (0.5 mg/ml and 1.0 mg/ml) and both temperatures (37° C. and 60° C.) tested on such layers. SEM analyses of the HA seed layered surface structures after immersion in Tobramycin-doped PBS for 6 days: a) 0.5 mg/ml Tobramycin at 37° C.; b) 1.0 mg/ml Tobramycin at 37° C.; c) 0.5 mg/ml Tobramycin at 60° C.; and d) 1.0 mg/ml Tobramycin at 60° C. show the morphology of the co-precipitated coatings was influenced by the PBS temperature. The morphology of the samples immersed in PBS of 37° C. appeared to be covered by a smooth and needle-like coating. See FIGS. 5(a) and 5(b). For both concentrations at 37° C. a coating thickness of approximately 5 µm was observed. Whereas, for the coating grown at concentrations of 0.5 mg/ml and 1.0 mg/ml in PBS temperatures of 60° C., a thinner coating of about. 1.5 µm and rougher, ball-like morphology appeared to have a more inhomogeneous structure. See FIGS. 5(c) and 5(d).

FIGS. 6(a)-6(f) show the impact of elevated temperatures (60° C.) and increased Tobramycin concentrations of (4 mg/ml and 20 mg/ml) on coating growth, where each is a a SEM analyses of the surface structures after immersion in Tobramycin-doped PBS for 6 days at 60° C.—a) without HA seed layer at 4 mg/ml; b) and c) with HA seed layer at 4 mg/ml (different magnifications); d) without HA seed layer at 20 mg/ml; and e) and f) with HA seed layer at 20 mg/ml (different magnifications).

Figure 6A:
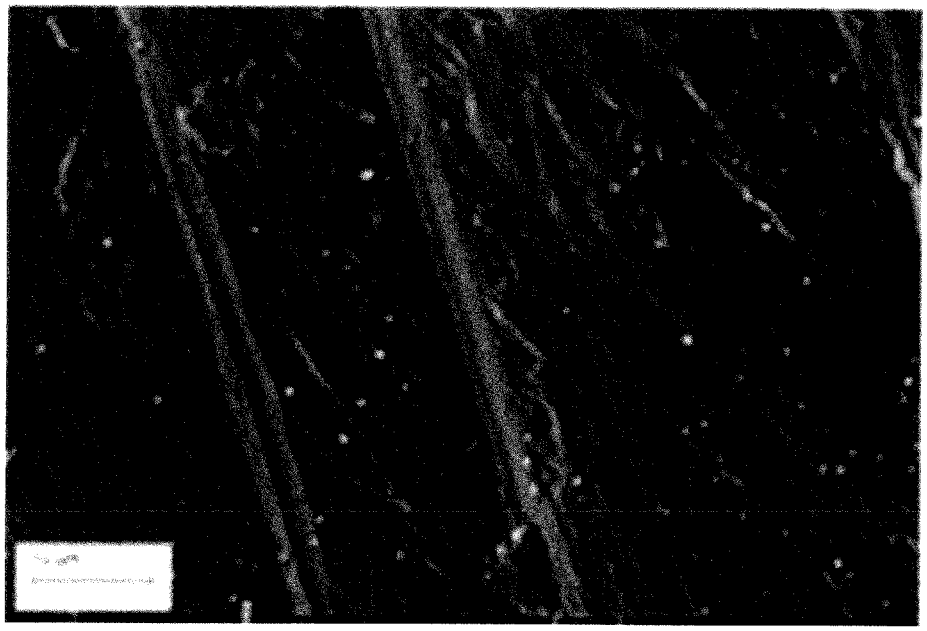
FIGS. 6(a)-6(f) are SEM images of the surface structures after immersion in Tobramycin-doped PBS for 6 days at 60° C. a) without the HA seed layer at 4 mg/ml; b) and c) with HA seed layer at 4 mg/ml at different magnifications; d) without HA seed layer at 20 mg/ml; and e) and f) with HA seed layer at 20 mg/ml at different magnifications.
Figure 6B:
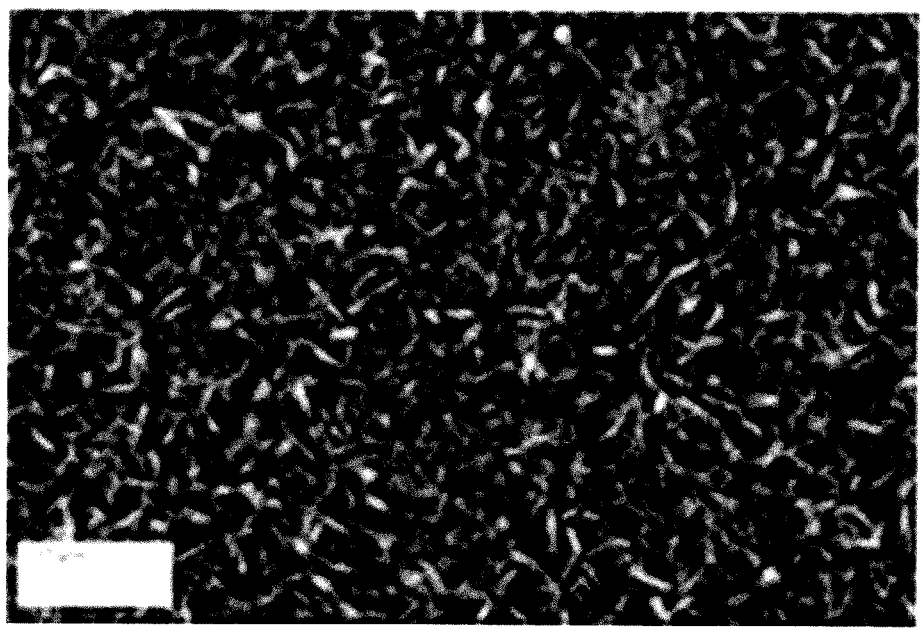
Figure 6C:
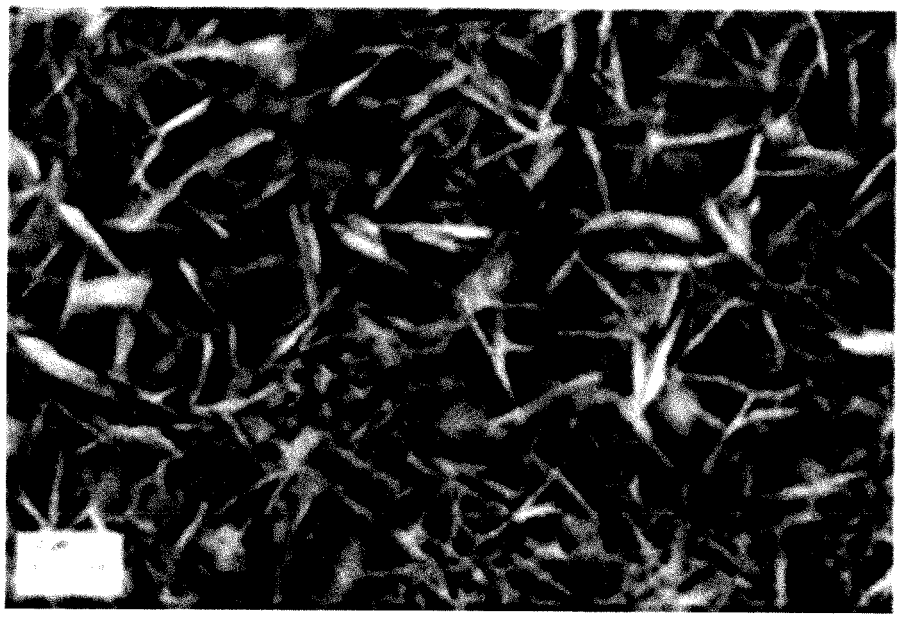
Figure 6D:
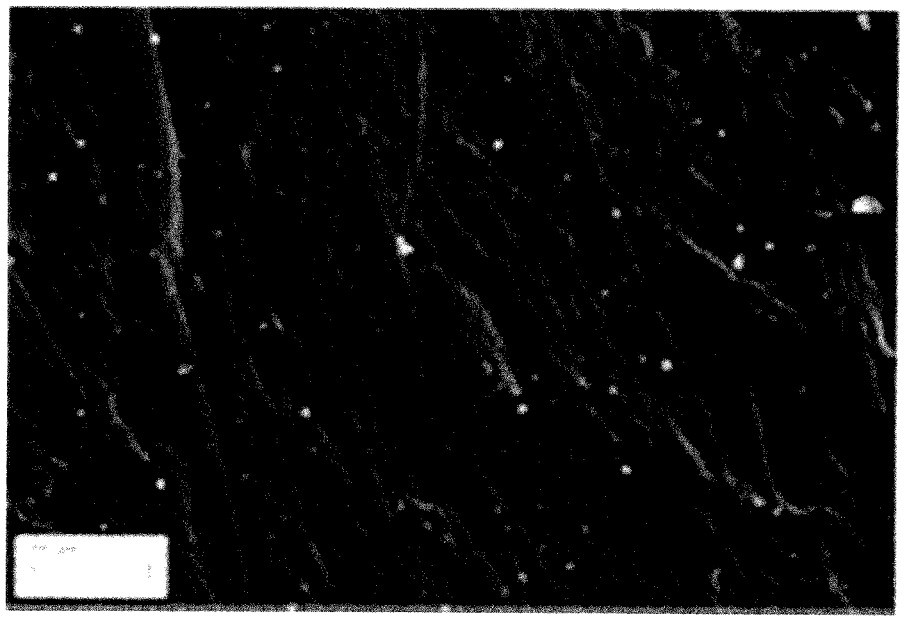
Figure 6E:
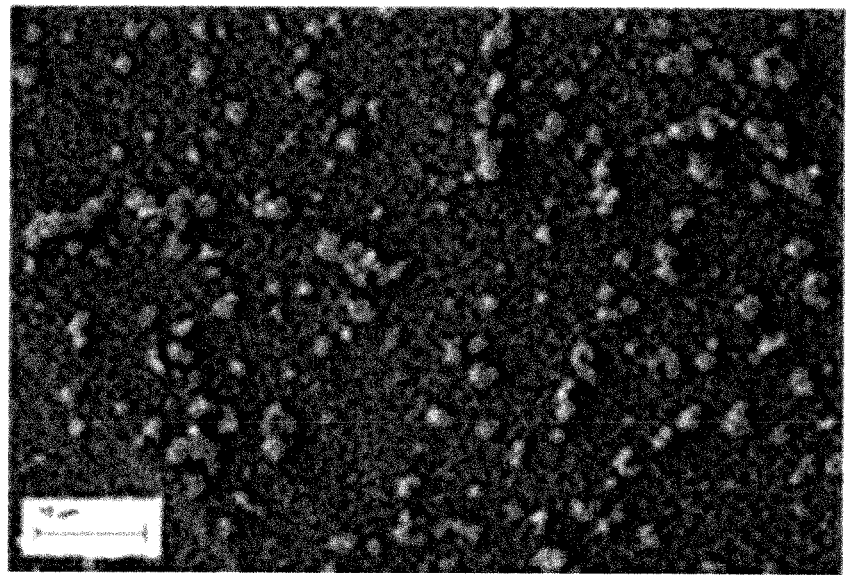
Figure 6F:
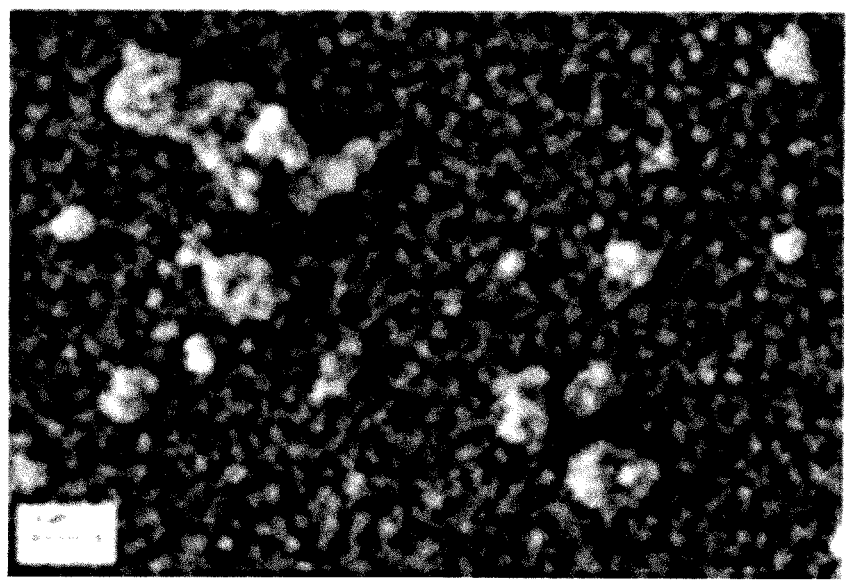

The reference discs without an HA seed layer showed no sign of nucleation at the selected temperature and Tobramycin concentrations, as shown in FIGS. 6(a) and 6(d), while the presence of the seed layer resulted in Tobramycin-doped HA growth for both concentrations, as shown in FIGS. 6(b), (c), (e) and (f). Different concentrations of Tobramycin in the PBS resulted in slightly different morphologies of the produced coatings. The coatings made using 4 mg/ml of the drug had a growth after storage for 6 days at 60° C. that resulted in coating thicknesses of about 4 µm with a needle-like morphology, FIG. 6(c). However, the coatings produced at the higher drug concentration had thicknesses of about 3 µm and contained ball-like agglomerates with a more dense and rough surface topography, FIG. 6(e). The measured thicknesses reported includes the thickness of the HA start layer of about 300 to about 600 nm.

Figure 7A:
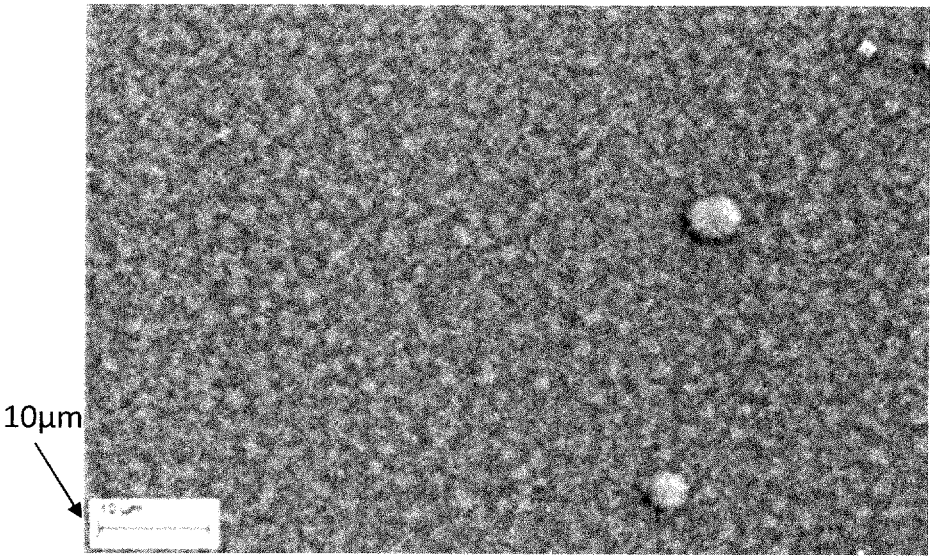
FIGS. 7(a)-7(b) are SEM images of the HA seed layered surface structures after immersion in Tobramycin-doped PBS for 6 days with a) 4 mg/ml Tobramycin at 37° C.; b) 20 mg/ml Tobramycin at 37° C.
Figure 7B:
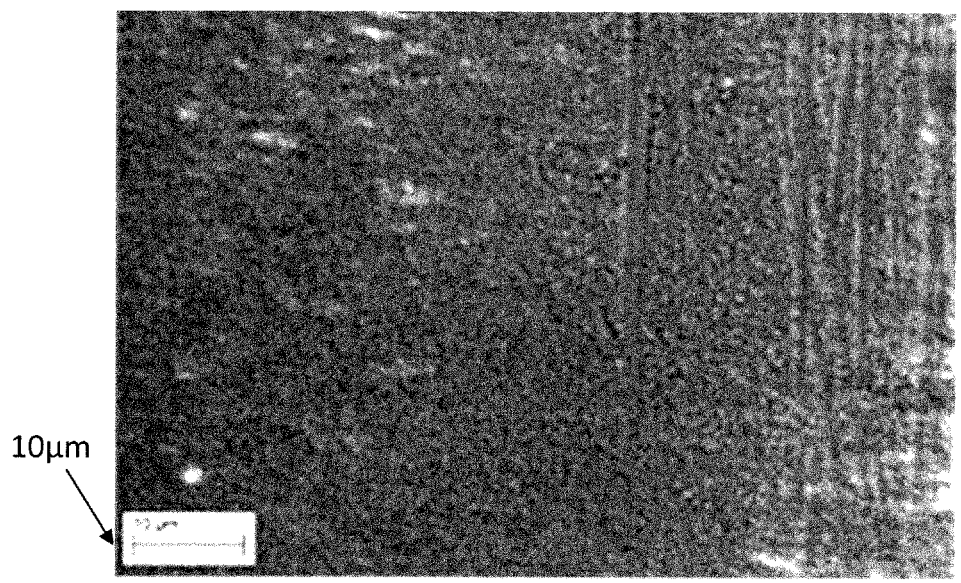

The co-precipitation coating technique was successfully transferred from discs to fixation pins. To achieve a homogeneous morphology and smooth surface topography, the HA seed layered fixation pins were tested at concentrations of 4 mg/ml and 20 mg/ml at with the lower deposition temperature of 37° C. to produce the pin coatings on top of the HA seed layer. The decreased temperature of 37° C. resulting in a nucleation of Tobramycin-doped HA at both concentrations. Referring to FIGS. 7(a)-7(b), a continuous Tobramycin-doped HA-coating could be observed for both antibiotic concentrations tested (4 and 20 mg/ml), fully covering the complex pin geometry, FIGS. 7(a) and (b). The co-precipitated HA coating morphology changed from flake-like (4 mg/ml), FIG. 7(a), towards smaller, spherical crystals (20 mg/ml), FIG. 7(b), in accordance with the results observed for the discs at the higher deposition temperature, as shown in FIGS. 6(a)-(e).

The total coating thickness (including the start layer) was measured from about 3 to about 3.5 µm for Tobramycin concentrations of 4 mg/ml and decreased to about 2 to about 2.5 µm for the increased drug concentration of 20 mg/ml.

An overview of the sample process parameters, coating thicknesses and coating appearance is shown in Table 1.

TABLE 1

| Sample type | Process time [d] | Process temperature [° C.] | HA seed layer | Tobramycin concentration [mg/ml] | Coating thickness [µm] | Coating appearance |
|---|---|---|---|---|---|---|
| Disc | 6 | 37 | No | 40 | — | — |
|  | 6 | 37 | No | 20 | — | — |
|  | 6 | 37 | No | 4 | — | — |
| Disc | 6 | 37 | No | 1 | — | — |
|  | 6 | 37 | No | 0.5 | — | — |
|  | 6 | 60 | No | 1 | ~1.5 | Ball-like |
|  | 6 | 60 | No | 0.5 | ~1.5 | Ball-like |
| Disc | 6 | 37 | Yes | 1 | ~5.0 | Needle-like |
|  | 6 | 37 | Yes | 0.5 | ~5.0 | Needle-like |
|  | 6 | 60 | Yes | 1 | ~1.5 | Ball-like |
|  | 6 | 60 | Yes | 0.5 | ~1.5 | Ball-like |
| Disc | 6 | 60 | No | 20 | — | — |
|  | 6 | 60 | No | 4 | — | — |
|  | 6 | 60 | Yes | 20 | ~3.0 | Ball-like |
|  | 6 | 60 | Yes | 4 | ~4.0 | Needle-like |
| Fixation Pin | 6 | 37 | Yes | 20 | ~2.5 | Ball-like |
|  | 6 | 37 | Yes | 4 | ~3.5 | Needle-like |

Figure 7C:
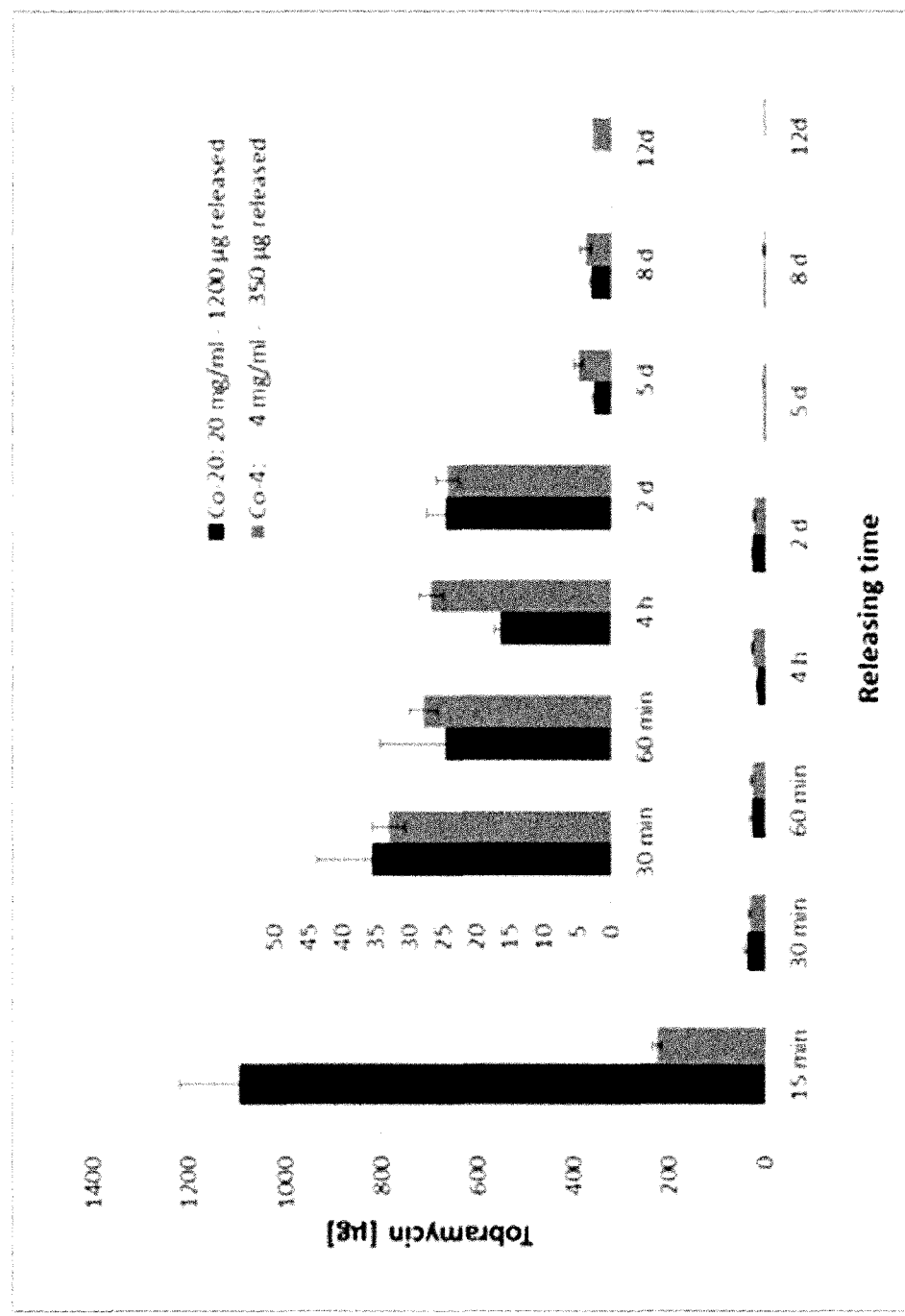
FIG. 7(c) is a graph of the non-cumulative amount of Tobramycin released in 37° C. PBS from co-precipitated pins with different concentrations of Tobramycin in PBS solution via HPLC.

In addition to SEM evaluation, the Tobramycin release profiles from the co-precipitated fixation pins were evaluated by HPLC. FIG. 7(c) presents the release kinetics from the co-precipitated fixation pins (Tobramycin release in µg/fixation pin) over a time period of 12 days. In general, the release profile is characterized by an initial burst followed by a sustained release for all three sample types studied with a total concentration released into the 5 ml PBS solution above the MIC of Staphylococcus aureus. The total amount of drug released from Co-4 samples was about 350 µg/pin, whereas a significantly higher release was measured for Co-20 samples with a total amount of 1200 µg/pin.

The major part of the drug content in the coatings, 226 µg and 1093 µg for Co-4 and Co-20 samples, respectively, was released during the initial 15 minutes. For both concentrations used to produce the coatings, the amount of drug released decreased significantly during the sustained release period. Co-20 showed slightly higher release values between 15 and 30 minutes as compared to the Co-4, whereas the Co-4 samples provided higher release values at all later time points excepting the 2 day time point where the amounts released were nearly equal for both sample types. No release could be detected from the Co-20 samples after 8 days while the Co-4 samples continue to provide a measurable amount of Tobramycin release up to 12 days.

Additionally, the samples Co-4/20 produced by co-precipitation at 4 mg/ml followed by fast adsorptive loading in a 20 mg/ml Tobramycin stock solution demonstrated an enhanced initial burst compared to the Co-4 samples, which was comparable to the initial release seen from Co-20 samples. During the sustained release period, the Co-4/20 samples overall provided a higher amount of drug release compared to both other sample types.

Figure 8C:
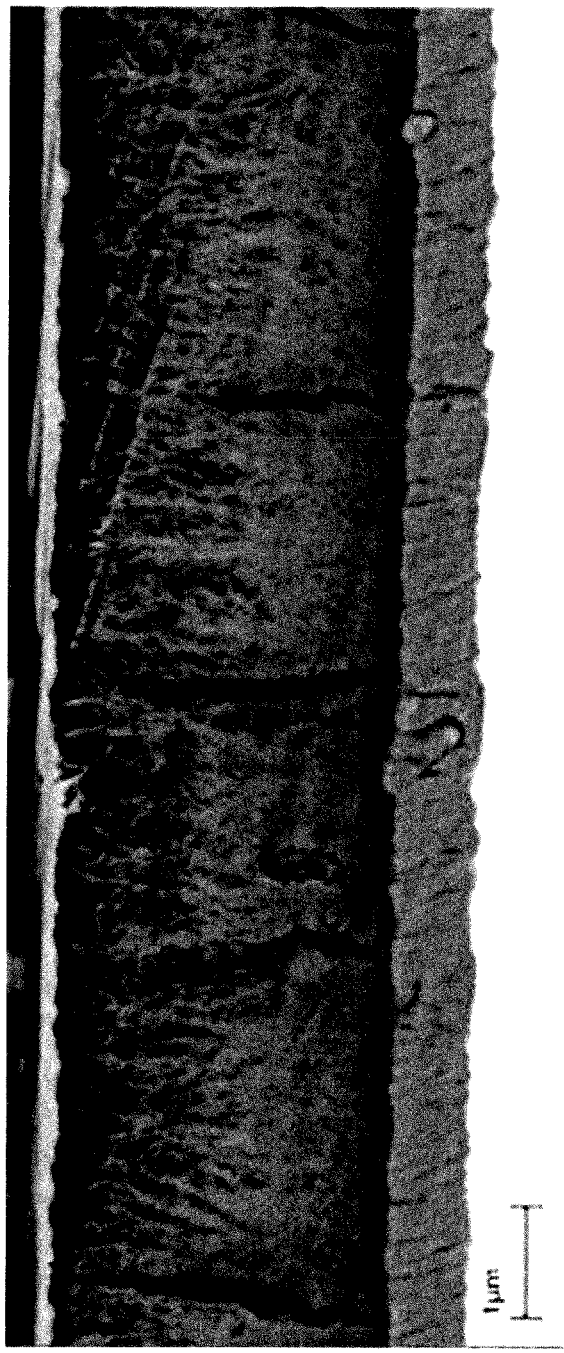
FIG. 8(c) is an SEM image of Tobramycin-doped HA.

The carbon and nitrogen depth profiles obtained from GD-OES measurements of co-precipitated Co-4 discs are shown in FIG. 8(*a*) 8(*b*) and compared to a pure, non-antibiotic containing biomimetic HA-coating (HA-ref) with a thickness of about 5 μm. SEM cross-section analysis demonstrate a sample coating thickness of about 3 μm, whereas the HA seed layer, as in FIG. 4, had a thickness of about 300 to about 600 nm. The coating morphology showed the previously described needle-like structure and appeared to be denser towards the bioactive, crystalline $TiO_2$ surface, FIG. 8 (*b*). Several cracks were detected within the cross-section of the measured sample, which can most likely be related to mechanical forces being activated as part of the preparation technique.

Both, C- and N-concentrations increased from the substrate interface towards the surface. The C-depth profile showed an increased weight fraction of carbon in Co-4 throughout the entire coating thickness of about 3 μm, compared to the reference (HA-ref) showing that co-precipitation enabled to integrate the drug throughout the entire coating. Likewise, the N-depth profile demonstrated increased nitrogen concentration for Co-4 for the outmost approximate 1.2 μm of the coating compared to HA-ref. From about 1.2 to about 1.8 μm, the nitrogen concentration demonstrates nearly equal values followed by slightly higher concentrations towards the substrate interface. The highest C- and N-concentrations were detected on the outer surface and may most likely originate from superficially adsorbed drug containing solution.

Given the above, the feasibility to co-precipitate pharmaceutically relevant doses of Tobramycin during biomimetic coating deposition has been shown. The process of HA crystallization on bioactive substrates is strongly affected by the concentration of drugs to be incorporated in PBS, as well as the process temperature. The presence of Tobramycin in PBS resulted in a decreased coating thickness compared to pure biomimetically deposited HA coatings. An elevated PBS temperature produced drug containing coatings for concentrations up to 1.0 mg/ml with rough ball-like morphology.

It has been shown that at higher process temperature increased ion mobility can be expected, which can contribute to enhance HA nucleation and growth. This supports the coating growth observed at increased temperature even in the presence of minor amounts of Tobramycin. In comparison, lower process temperatures in combination with higher concentrations of Tobramycin seemed to inhibit crystallization of HA on $TiO_2$ substrates. This could be explained by the fact that Tobramycin could act as an anticatalyst for the HA nucleation process under these conditions. The Tobramycin-induced inhibition of nucleation seems to decrease at higher temperatures and lower concentrations. At these conditions the solubility product of HA seems to be exceeded and thus, nucleation of HA seed crystals can occur. Nevertheless, a combination of higher ion mobility and changes in solubility products may affect the differences in crystallization observed. This assumption may also explain the impact of the HA start layer on coating growth in the presence of Tobramycin. The HA coating might act like a seed crystal for all following coating growth steps and, hence, facilitate HA growth at lower process temperatures and higher concentrations of Tobramycin.

SEM analysis demonstrated needle-like morphology for Co-4 coatings grown at 37° C. Coatings deposited at elevated temperature and in the presence of minor amounts of Tobramycin showed a change in morphology from needle- to ball-like appearance. A comparable change in morphology was observed in case of increased Tobramycin concentrations where, in addition, the formation of agglomerates on the coating surface was observed. Thus, it may be concluded that Tobramycin influences the morphology of the coating grown during co-precipitation. At a critical antibiotic concentration, nucleation and growth might be limited and even inhibited as supported by the decrease in coating thickness and morphology with increasing drug concentrations. Elevated process temperature on the other hand improves nucleation and growth up to Tobramycin concentrations of 1 mg/ml, which may be attributed to the previously described impact of temperature on the growth kinetics. Furthermore, high drug concentrations could lead to drug-drug interactions during the adsorption and crystallization processes, which minimize the chances of nucleation.

It can be noted that Tobramycin has an effect on the development of the co-precipitated coating itself and can be classified as an impact factor for growth even in the presence of an HA start layer. The deposition of a sub-micron thin HA start layer allowed for incorporation of higher concentrations of Tobramycin during coating growth. Tobramycin may have a higher binding energy to HA compared to $TiO_2$ which, hence, allows for co-precipitation at high drug concentrations even at low temperatures. The HA coating thickness supports the speculated preferential binding of Tobramycin to HA by an increased thickness. The release profile demonstrated an enhanced release period of 12 days. The released amounts of Tobramycin were found above the MIC of *Staphylococcus aureus*. These values were measured under sink conditions in PBS, which provide suitable in vitro conditions for evaluating the application of antibiotic releasing coatings in the fields of medical implants.

Co-precipitated samples released comparable amounts of drug during the initial burst period, as did adsorptively loaded samples made using similar concentrations of drugs. Nevertheless, the sustained release period showed superior amounts of drug released from co-precipitated samples. GD-OES measurements confirmed the drug incorporation throughout the entire coating thickness and, hence, an increased amount of drug released can be expected during the sustained release period originating of drug released from deeper and denser sections of the coating.

The nanoporous structure of co-precipitated coatings revealed the ability to incorporate higher amounts of antibiotic by additional adsorptive loading. Thus, the deposition of co-precipitated coatings allows for additional action in order to design release profiles targeting drug release for specific applications.

The presented coating deposition method does not only allow to incorporate pharmaceutically relevant amounts of drug in a single step approach, in addition the release properties are superior to those previously reported and are expected to provide an enhanced antibacterial effect exceeding the 3 day benchmark reported in literature.

In summary, the starting phase of crystallization presents a very important part for coating deposition using the co-precipitation approach. Surface chemistry, as well as process temperature, are important factors that have been shown to impact coating growth, thickness and the morphology of drug-doped HA coatings.

A promising innovative co-precipitation approach demonstrated feasibility to create a Tobramycin-doped HA coating delivering pharmaceutically relevant amounts of drugs over a period of 12 days. The release period is superior compared to earlier presented results from biomimetic HA coatings loaded by fast-soaking approaches. The Tobramycin-doped HA coating was achieved by pre-covering the surface with a sub-micron, thin, pure HA layer to trigger co-precipitation even at high drug concentrations and low (37° C.) process temperatures. The release mechanism showed a controllable high initial burst release followed by a continuous sustained release. The total amount of drug released was above the MIC of *Staphylococcus aureus*. The nanoporous structure of the investigated co-precipitated coatings furthermore allowed for tailoring of the drug release profile by additional adsorptive loading. The elution kinetic and the concentrations of Tobramycin released over time from the co-precipitated coatings can prevent against early bacterial colonization and biofilm formation at the time of surgery and post-operatively.

Such a process method allows, not only, coating of complex implant geometries, but also delivery of ready-to-use antibiotic-doped HA implants to the surgeon. The herein presented results demonstrate a fundamental base for future development combining adequate antibiotic delivery with a special clinical need. After careful evaluation of pharmaceutically relevant problems, this type of coating could be used to develop a special implant addressing these needs. The performance of the co-precipitated HA coating and its ability to promote faster osseointegration and prevent infection can be confirmed in-vivo.

Although the present embodiments have been described in relation to particular aspects thereof, many other variations and modifications and other uses will become apparent to those skilled in the art. It is preferred therefore, that the present disclosure be limited not by the specific embodiments herein, but only by the appended claims.

What is claimed is:

1. A method for co-precipitating a therapeutic agent into a hydroxyapatite coated surface comprising the steps of:
   providing a surface which includes a coating selected from the group of $TiO_2$, $TiO$, $TiCrO_2$, $Ti_2O_3$, $Ti_3O_5$, $SiO_2$, $MgO_2$, $AlO_2$, $MgO$, $Al_2O_3$, and $CrO_2$;
   applying a hydroxyapatite seed layer having a thickness of 0.1 μm to 1 μm on the surface;
   contacting the hydroxyapatite seed layered surface with a solution including the therapeutic agent; and
   forming a co-precipitated therapeutic agent, hydroxyapatite layer on the coated surface to uniformly distribute the therapeutic agent in the layer.

2. A method according to claim 1, wherein the therapeutic agent is selected from the group of antibiotics, vitamins, chemotherapy drugs, bisphosphonates, strontium ranelate, PTH, osteoporotic drugs, growth factors, or a combination thereof.

3. A method according to claim 1, wherein the surface is a material selected from the group of titanium, titanium alloy, nickel-titanium alloy, tantalum, platinum-iridium alloy, gold, magnesium, stainless steel, chromo-cobalt alloy, ceramics, biocompatible plastics or polymers and combinations thereof.

4. A method according to claim 1, wherein the hydroxyapatite seed layer is grown biomimetically.

5. A method according to claim 1, wherein the co-precipitated therapeutic agent, hydroxyapatite layer is grown biomimetically.

6. A method according to claim 1, wherein the thickness of the co-precipitated layer is of 1 μm to 10 μm.

7. A method according to claim 1, wherein the therapeutic agent in the solution including the therapeutic agent has a concentration of 0.5 to 40 mg/ml.

8. A method according to claim 1, wherein the co-precipitated therapeutic agent, hydroxyapatite layer and the seed layer are ion substituted hydroxyapatite.

9. A method according to claim 8, wherein the substitution ions are bone mineral relevant ions.

10. A method according to claim 8, wherein the substitution ions are selected from the group of Si, Sr, Mg, C02-3, and F ions.

11. A method according to claim 1, wherein the solution including the therapeutic agent is heated to a temperature of about 30° C. to about 90° C.

12. A method according to claim 11, wherein the temperature is 60° C.

13. A method according to claim 1, wherein the seed layer is applied by soaking the surface in phosphate buffered saline solution containing calcium and phosphate ions.

14. A method according to claim 13, wherein the phosphate buffered saline solution has a temperature of from 30 to 90° C.

15. A method according to claim 14, wherein the phosphate buffered saline solution has a temperature of 60° C.

16. A hydroxyapatite coated surface co-precipitated with a therapeutic agent according to the method of claim 1.

17. A device having a hydroxyapatite coated surface co-precipitated with a therapeutic agent according to the method of claim 1.

18. The device of claim 17, wherein the device is selected from the group of implants, pins, fixation pins, orthopedic devices, dental implants, stents, drug delivery devices, sheets, films, meshes, soft tissue implants, implantable electrodes, implantable sensors, drug delivery pumps, tissue barriers and shunts.

* * * * *